United States Patent
Richer et al.

(10) Patent No.: US 11,564,614 B2
(45) Date of Patent: Jan. 31, 2023

(54) SYSTEMS AND METHODS FOR IDENTIFYING ABLATION LOCATIONS USING ELECTRICAL PARAMETER DATA

(71) Applicant: St. Jude Medical, Cardiology Division, Inc., St. Paul, MN (US)

(72) Inventors: Louis-Philippe Richer, Montreal (CA); Chunlan Jiang, Northridge, CA (US); Craig Markovitz, Mahtomedi, MN (US); Jan Mangual, Rho (IT); Cyrille Casset, Saint Selve (FR)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 146 days.

(21) Appl. No.: 17/061,961

(22) Filed: Oct. 2, 2020

(65) Prior Publication Data
US 2021/0128006 A1    May 6, 2021

Related U.S. Application Data

(60) Provisional application No. 62/927,796, filed on Oct. 30, 2019.

(51) Int. Cl.
*A61B 5/339*   (2021.01)
*A61B 5/364*   (2021.01)
*A61B 5/283*   (2021.01)

(52) U.S. Cl.
CPC ............ *A61B 5/364* (2021.01); *A61B 5/283* (2021.01); *A61B 5/339* (2021.01)

(58) Field of Classification Search
CPC ................ A61B 5/367; A61B 5/339; A61B 2018/00839
See application file for complete search history.

(56) References Cited

U.S. PATENT DOCUMENTS

| | | | |
|---|---|---|---|
| 7,255,695 B2 | 8/2007 | Falwell et al. | |
| 8,498,686 B2 | 7/2013 | Grunewald | |
| 9,295,398 B2 | 3/2016 | Greenspan | |
| 9,655,535 B2 | 5/2017 | Narayan et al. | |
| 10,092,196 B2 | 10/2018 | Narayan et al. | |
| 2014/0200467 A1* | 7/2014 | Strom | A61B 5/0044 600/300 |

* cited by examiner

*Primary Examiner* — George R Evanisko
(74) *Attorney, Agent, or Firm* — Armstrong Teasdale LLP

(57) ABSTRACT

Systems and methods for identifying potential ablation sites using electrical parameter data are provided. A method includes geometrically isolating an arrhythmogenic substrate in a three-dimensional geometry. The method further includes generating a first cumulative map from a first dataset including electrical parameter data for each vertex in the isolated arrhythmogenic substrate, and generating a second cumulative map from a second dataset including additional data for each vertex. The method further includes generating a third cumulative map from the first and second cumulative maps, and displaying the third cumulative map on the three-dimensional geometry to facilitate identifying potential ablation sites.

20 Claims, 8 Drawing Sheets

FIG. 5

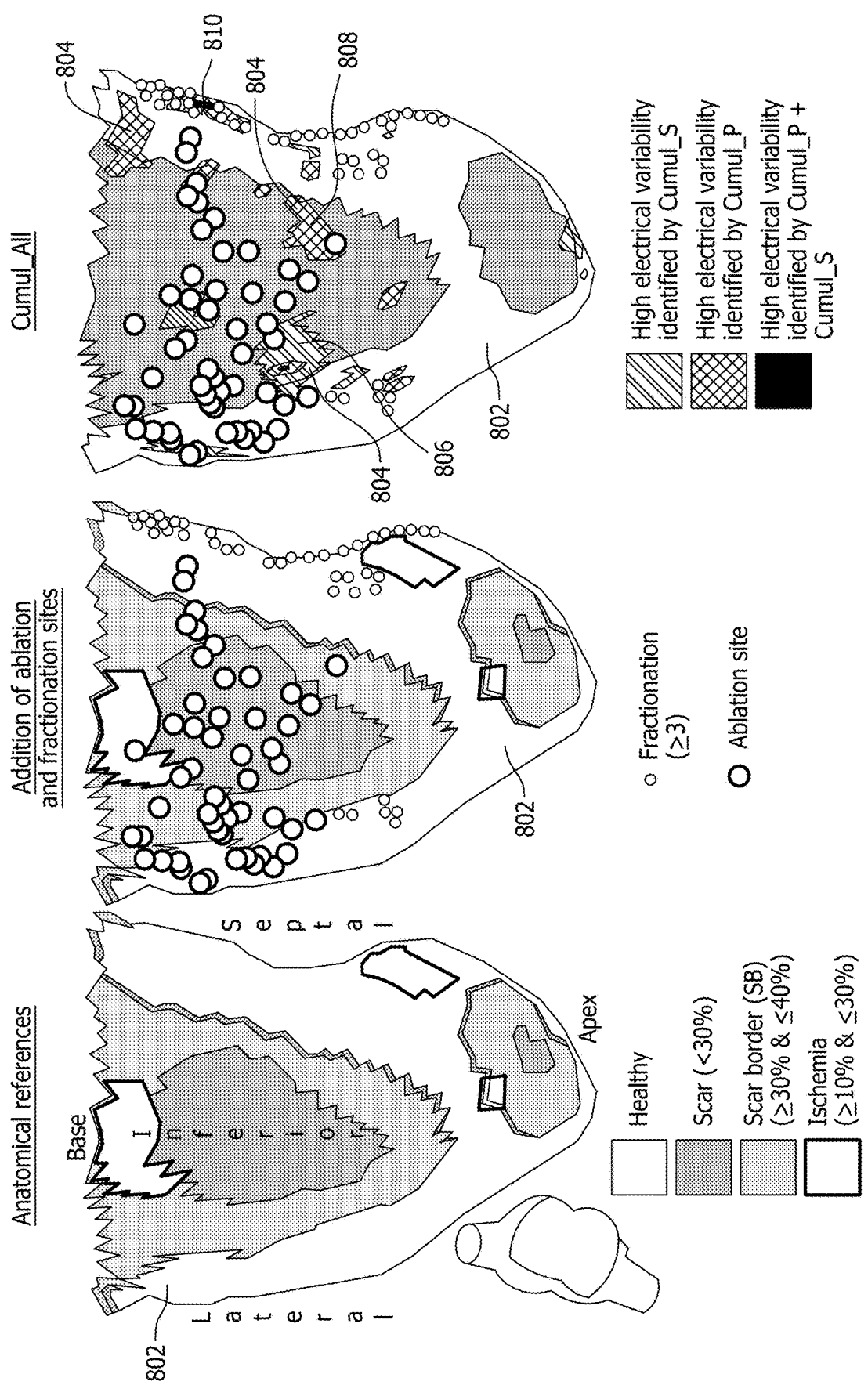

SYSTEMS AND METHODS FOR IDENTIFYING ABLATION LOCATIONS USING ELECTRICAL PARAMETER DATA

CROSS REFERENCE TO RELATED APPLICATIONS

This application claims priority to provisional application Ser. No. 62/927,796, filed Oct. 30, 2019, which is incorporated herein by reference in its entirety.

FIELD OF THE DISCLOSURE

The present disclosure relates generally to tissue ablation systems. In particular, the present disclosure relates to identifying potential ablation locations using electrical parameter data.

BACKGROUND

Radiofrequency (RF) ablation is often an effective treatment strategy for patients with ventricular tachycardia (VT). To improve efficacy of RF ablation, it is generally desirable to identify locations that, when ablated, will likely reduce VT. For example, when VT is not inducible or not hemodynamically tolerated, a clinician may attempt to identify a VT substrate for ablation during a stable sinus or paced rhythm.

It has been established that arrhythmogenic substrates are closely related to sudden cardiac death in patients. However, the origin and involvement of the substrate in arrhythmias is relatively complex, multifactorial, and often the result of an interplay between an anatomical substrate (e.g., mixtures of viable myocytes and non-viable fibrous tissue, neural imbalance, lack of perfusion, etc.) and transient triggers leading to electrical instability (e.g., low voltages zones, signal fractionation, etc.) including increased automaticity, triggered activity, and re-entry. Such a substrate, particularly at a border zone where conductive tissue is adjacent to non-conductive scar tissue, is important for arrhythmia initiation and maintenance. Further, the mixture of different pro-arrhythmic factors in the substrate may vary significantly between patients, making it more difficult to understand.

Improvements in imaging modality technologies enable collecting additional data (e.g., tissue perfusion, metabolic status, innervation, presence of fibrosis, etc.) on a pro-arrhythmic substrate. However, tools allowing analysis of the border zone of the arrhythmogenic substrate in the ventricle have yet to be developed for electro-anatomical mapping, one of the more widely used technologies for aiding in ablation therapy delivery. In at least some existing systems, when using electro-anatomical mapping, the physician is responsible for investigating the cardiac tissue, mentally compiling various electrical maps, and determining ablation locations.

However, this may result in the physician choosing ablation locations to pursue scar homogenization instead of targeted ablations. Although pursuing scar homogenization may free patients from arrhythmic episodes, targeted ablations are generally more efficient. Further, scar homogenization techniques may take a relatively long time, and a relatively large number of patients (e.g., over 50%) may need to return for additional ablation procedures. Accordingly, it would be desirable to incorporate electrical parameter data to determine suggested ablation locations for a clinician.

BRIEF SUMMARY OF THE DISCLOSURE

In one embodiment, the present disclosure is directed to a computer-implemented method for identifying potential ablation sites using electrical parameter data. The method includes geometrically isolating, using a computing device, an arrhythmogenic substrate in a three-dimensional geometry, the three-dimensional geometry including a plurality of vertices. The method further includes generating, using the computing device, a first cumulative map from a first dataset, the first dataset including electrical parameter data for each vertex in the isolated arrhythmogenic substrate, and generating, using the computing device, a second cumulative map from a second dataset, the second dataset including additional data for each vertex in the isolated arrhythmogenic substrate, the additional data derived from the electrical parameter data. The method further includes generating, using the computing device, a third cumulative map from the first and second cumulative maps, and displaying, using the computing device, the third cumulative map on the three-dimensional geometry to facilitate identifying potential ablation sites.

In another embodiment, the present disclosure is directed to a computing device for identifying potential ablation sites using electrical parameter data. The computing device includes a memory device and a processor communicatively coupled to the memory device. The processor is configured to geometrically isolate an arrhythmogenic substrate in a three-dimensional geometry, the three-dimensional geometry including a plurality of vertices, generate a first cumulative map from a first dataset, the first dataset including electrical parameter data for each vertex in the isolated arrhythmogenic substrate, and generate a second cumulative map from a second dataset, the second dataset including additional data for each vertex in the isolated arrhythmogenic substrate, the additional data derived from the electrical parameter data. The processor is further configured to generate a third cumulative map from the first and second cumulative maps, and display the third cumulative map on the three-dimensional geometry to facilitate identifying potential ablation sites.

In yet another embodiment, the present disclosure is directed to non-transitory computer-readable media having computer-executable instructions thereon. When executed by a processor of a computing device, the instructions cause the processor of the computing device to geometrically isolate an arrhythmogenic substrate in a three-dimensional geometry, the three-dimensional geometry including a plurality of vertices, generate a first cumulative map from a first dataset, the first dataset including electrical parameter data for each vertex in the isolated arrhythmogenic substrate, and generate a second cumulative map from a second dataset, the second dataset including additional data for each vertex in the isolated arrhythmogenic substrate, the additional data derived from the electrical parameter data. The instructions further cause the processor to generate a third cumulative map from the first and second cumulative maps, and display the third cumulative map on the three-dimensional geometry to facilitate identifying potential ablation sites.

The foregoing and other aspects, features, details, utilities and advantages of the present disclosure will be apparent from reading the following description and claims, and from reviewing the accompanying drawings.

BRIEF DESCRIPTION OF THE DRAWINGS

FIG. 5 is a diagram illustrating an example dataset.

FIGS. 8A-8C illustrate a comparison between at least some known ablation determination techniques and the systems and methods described herein.

DETAILED DESCRIPTION OF THE DISCLOSURE

The present disclosure provides systems and methods for identifying potential ablation sites using electrical parameter data. A method includes geometrically isolating an arrhythmogenic substrate in a three-dimensional geometry. The method further includes generating a first cumulative map from a first dataset including electrical parameter data for each vertex in the isolated arrhythmogenic substrate, and generating a second cumulative map from a second dataset including additional data for each vertex. The method further includes generating a third cumulative map from the first and second cumulative maps, and displaying the third cumulative map on the three-dimensional geometry to facilitate identifying potential ablation sites.

The systems and method described herein involve collecting, analyzing, and displaying electrical parameter data (e.g., voltage measurements, local activation time measurements, and signal fractionation measurements) and additional data (e.g., descriptive statistics computed from the electrical parameter data) on a single map presented to a clinician. The techniques described herein facilitate uncovering regions of high variability in a border zone and/or in a core of an arrhythmogenic substrate. These regions of variability represent regions of electrical instability presumed to be associated with a mixture of viable and non-viable cardiac tissue. Accordingly, these regions correspond to potential ablation locations/sites.

Figure 1:
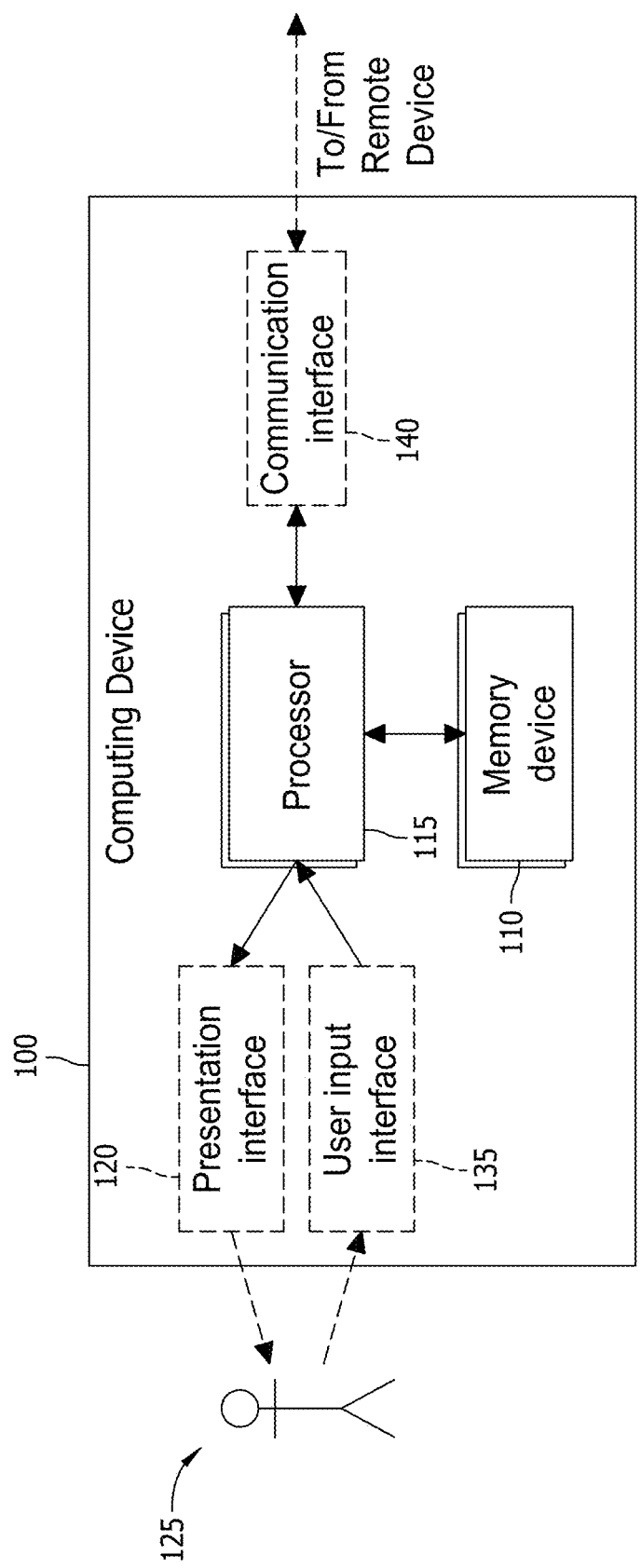
FIG. 1 is a block diagram of one embodiment of a computing device that may be used to implement the systems and methods described herein.

Referring now to the drawings wherein like reference numerals are used to identify identical components in the various views, FIG. 1 illustrates one embodiment of a computing device 100 that may be used to implement the systems and methods described herein. Computing device 100 includes at least one memory device 110 and a processor 115 that is coupled to memory device 110 for executing instructions. In some embodiments, executable instructions are stored in memory device 110. In this embodiment, computing device 100 performs one or more operations described herein by programming processor 115. For example, processor 115 may be programmed by encoding an operation as one or more executable instructions and by providing the executable instructions in memory device 110.

Processor 115 may include one or more processing units (e.g., in a multi-core configuration). Further, processor 115 may be implemented using one or more heterogeneous processor systems in which a main processor is present with secondary processors on a single chip. In another illustrative example, processor 115 may be a symmetric multi-processor system containing multiple processors of the same type. Further, processor 115 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In this embodiment, memory device 110 is one or more devices that enable information such as executable instructions and/or other data to be stored and retrieved. Memory device 110 may include one or more computer readable media, such as, without limitation, dynamic random access memory (DRAM), static random access memory (SRAM), a solid state disk, and/or a hard disk. Memory device 110 may be configured to store, without limitation, application source code, application object code, source code portions of interest, object code portions of interest, configuration data, execution events and/or any other type of data.

In this embodiment, computing device 100 includes a presentation interface 120 that is coupled to processor 115. Presentation interface 120 presents information to a user 125. For example, presentation interface 120 may include a display adapter (not shown) that may be coupled to a display device, such as a cathode ray tube (CRT), a liquid crystal display (LCD), an organic LED (OLED) display, and/or an "electronic ink" display. In some embodiments, presentation interface 120 includes one or more display devices. Input signals and/or filtered signals processed using the embodiments described herein may be displayed on presentation interface 120.

In this embodiment, computing device 100 includes a user input interface 135. User input interface 135 is coupled to processor 115 and receives input from user 125. User input interface 135 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of presentation interface 120 and user input interface 135.

Computing device 100, in this embodiment, includes a communication interface 140 coupled to processor 115. Communication interface 140 communicates with one or more remote devices. To communicate with remote devices, communication interface 140 may include, for example, a wired network adapter, a wireless network adapter, and/or a mobile telecommunications adapter.

As described in detail herein, computing device 100 executes an algorithm to identify potential ablation regions for a clinician. Specifically, computing device 100 processes electrical parameter data and additional data derived from the electrical parameter data to identify and display potential ablation locations, as described herein.

Figure 2:
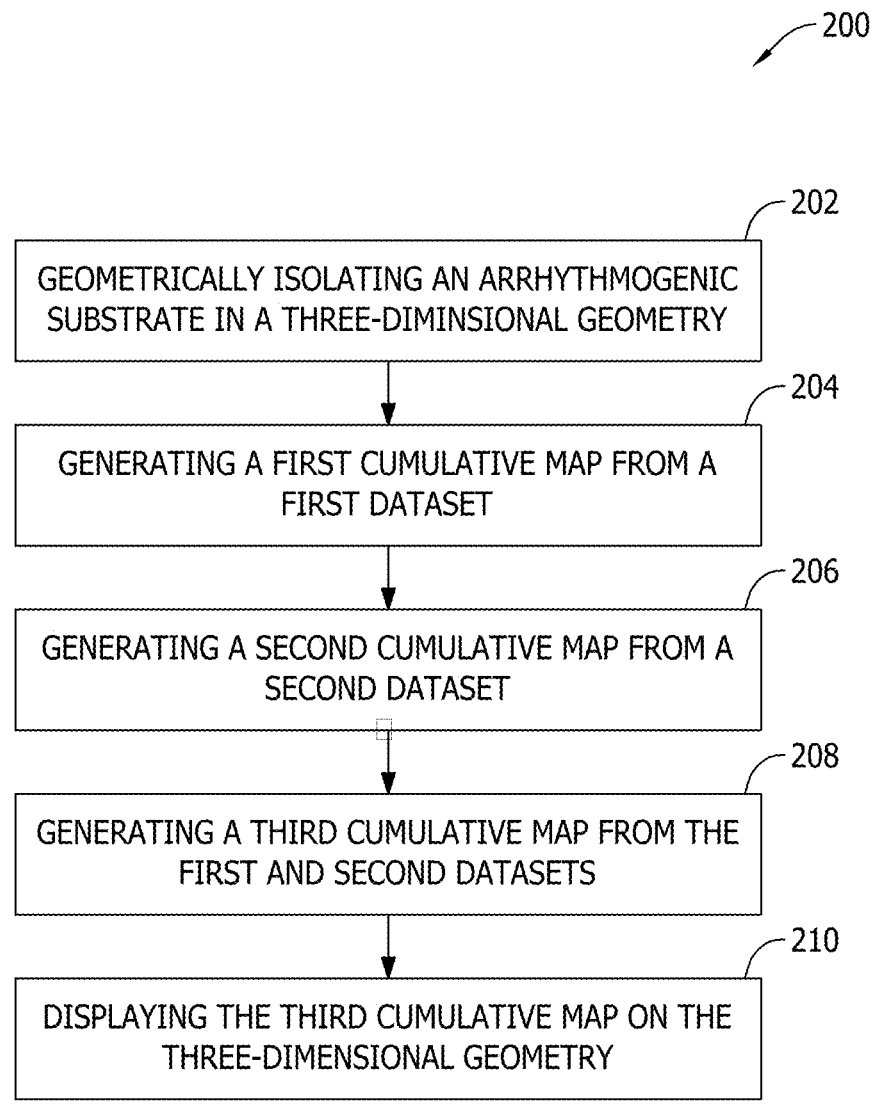
FIG. 2 is a block diagram of a method of identifying potential ablation locations using electrical parameter data.

FIG. 2 is a block diagram of a method 200 of identifying potential ablation locations using electrical parameter data. Method 200 may be implemented, for example, by computing device 100 (shown in FIG. 1). Method 200 includes geometrically isolating 202 an arrhythmogenic substrate in a three-dimensional geometry including a plurality of vertices. The three-dimensional geometry represents a cardiac chamber of interest, and may be generated using electro-anatomical mapping and/or imaging techniques (e.g., magnetic resonance imaging (MRI), computed tomography (CT), electrophysiological (EP) mapping, etc.).

Each vertex in the three-dimensional geometry is associated with electrical parameter data. For example, in one embodiment, values for voltage, local activation time, and fractionation are calculated and/or measured for each vertex. Further, for each type of electrical parameter data, additional data may be calculated. For example, for voltage, at a particular vertex, a mean voltage, voltage standard deviation, and voltage skewness may be calculated based on that vertex and neighboring vertices. Those of skill in the art will appreciate that voltage, local activation time, and fractionation are merely examples of electrical parameter data, and mean, standard deviation, and skewness are merely examples of additional data. Accordingly, those of skill in the art will appreciate that other types of electrical parameter data and additional data may be used in the systems and methods described herein.

The arrhythmogenic substrate may be geometrically isolated 202 by discarding vertices that have an electrical parameter or additional parameter value falling outside of a target range. For example, in one embodiment, vertices with a mean voltage value above a predetermined threshold (e.g., 1.6 millivolts (mV)) are discarded, while vertices with a mean voltage value less than or equal to the predetermined threshold are kept.

Figure 3:
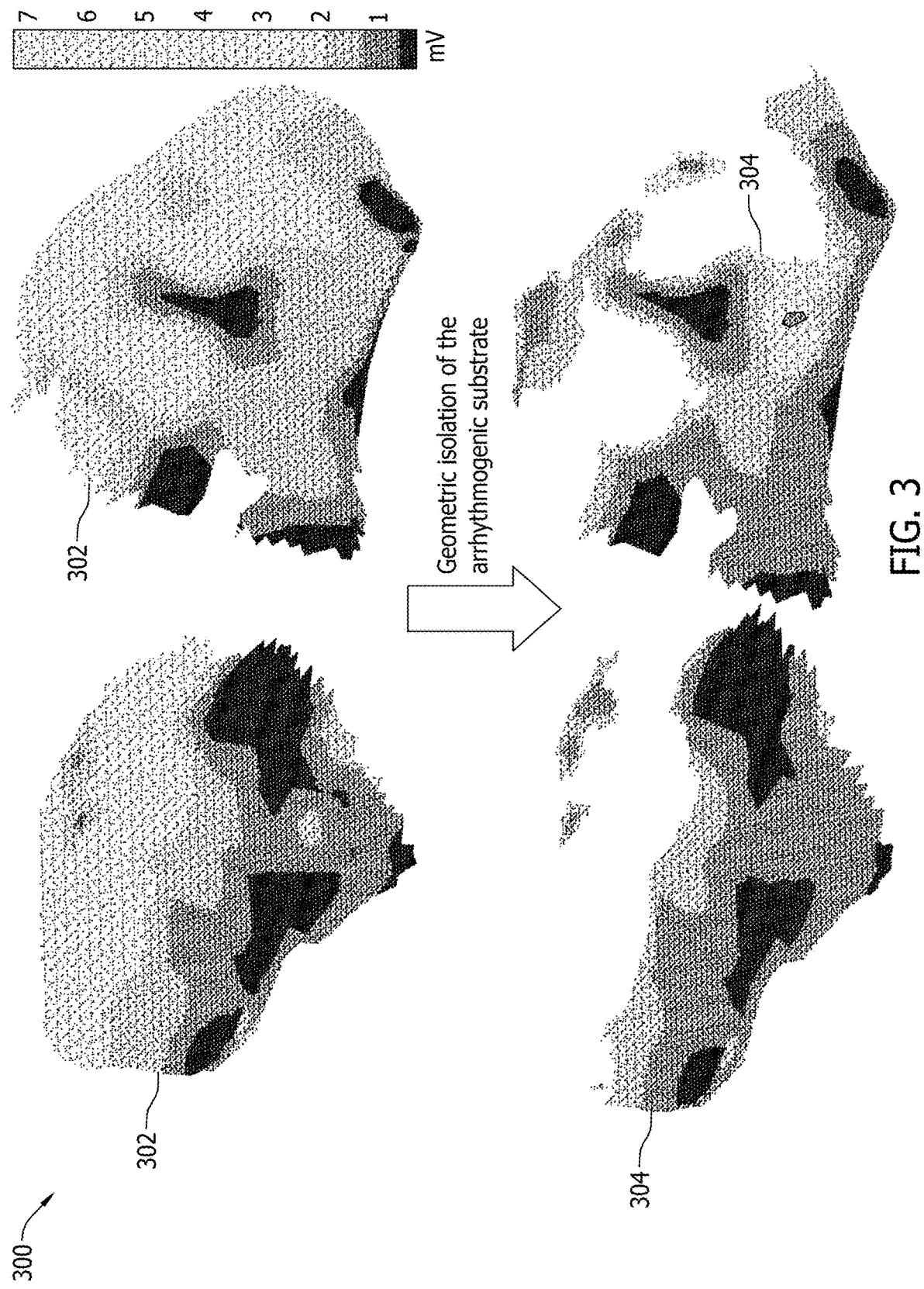
FIG. 3 is a diagram illustrating geometric isolation of an arrhythmogenic substrate.

FIG. 3 is a diagram 300 illustrating geometric isolation 202 of the arrhythmogenic substrate. As shown in FIG. 3, vertices with average voltage values above a predetermined threshold (in this example, 1.6 mV) are discarded from a three-dimensional geometry 302 to generate an isolated arrhythmogenic substrate 304.

The additional parameters variables may be generated by computing descriptive statistics for each vertex in the three-dimensional geometry. In one embodiment, the descriptive statistics are computed for each vertex based on all neighboring vertices within a predetermined radius of the particular vertex. The predetermined radius may be, for example, 0.5 centimeters (cm). Alternatively, any suitable predetermined radius may be used to compute the descriptive statistics.

Figure 4:
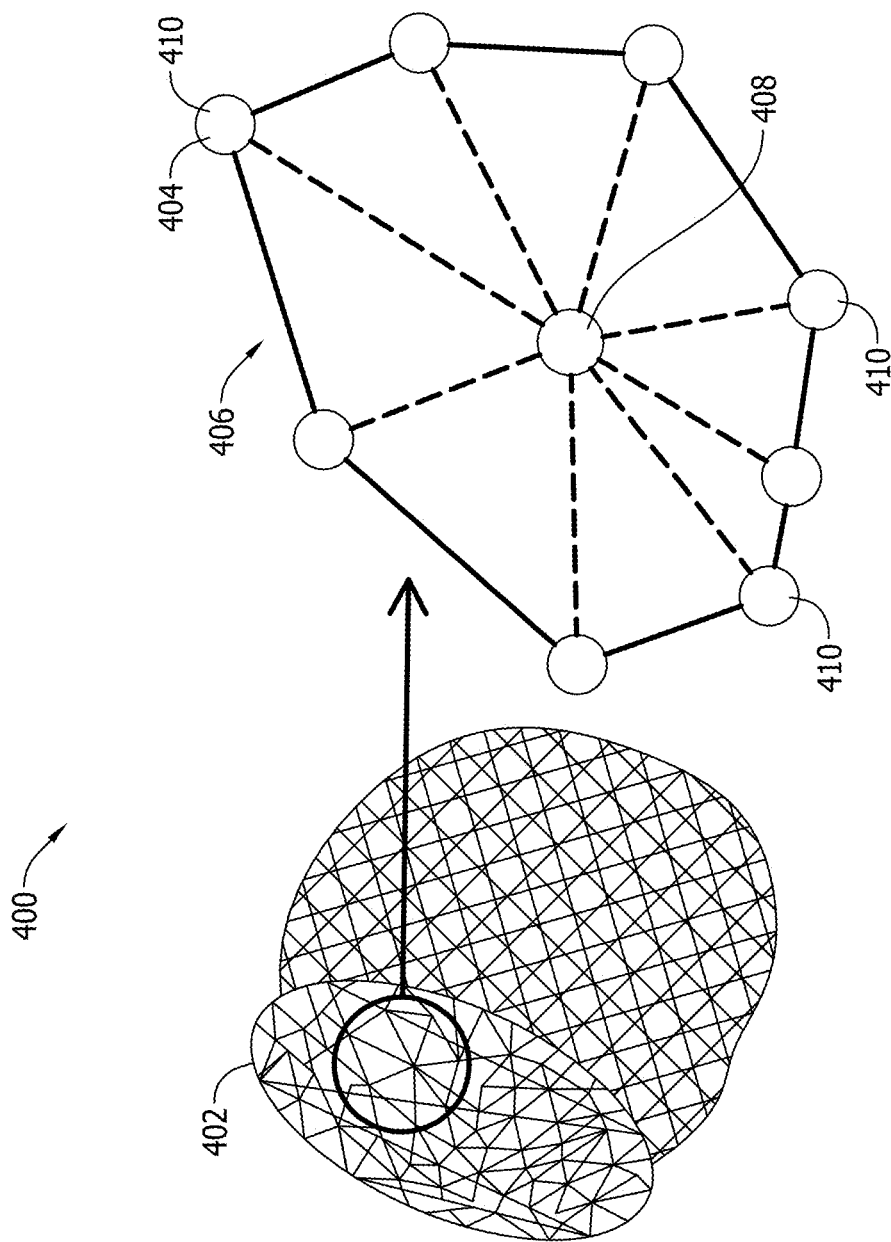
FIG. 4 is a diagram illustrating calculation of local descriptive statistics.

FIG. 4 is a diagram 400 illustrating calculation of local descriptive statistics. Specifically, diagram 400 shows a geometric mesh 402 generated using single-photon emission computed tomography (SPECT). Geometric mesh 402 is an example of a three-dimensional geometry. Geometric mesh 402 includes a plurality of vertices 404. An enlarged portion 406 of geometric mesh 402 is also shown in FIG. 4. Enlarged portion 406 includes a vertex of interest 408 (for which local descriptive statistics are calculated), and a plurality of neighboring vertices 410. Neighboring vertices 410 are vertices located within a predetermined radius (here, 0.5 cm) of vertex of interest 408. Because the distance between a vertex and its neighbors depends on its location in the mesh (e.g., vertices are generally closer to one another at the apex of the heart compared to the base), by keeping the analysis fixed to a predetermined radius, the number of neighboring vertices for each vertex may vary. Accordingly, in some embodiments, the descriptive statistics are computed for a fixed number of neighboring vertices for each vertex (instead of a fixed radius). In such embodiments, the location of the vertex will affect the size of the analysis area.

In this embodiment, the statistics calculated (i.e., the additional parameters) include mean voltage, voltage standard deviation, voltage skewness, mean local activation time, local activation time standard deviation, local activation time skewness, mean fractionation, fractionation standard deviation, and fractionation skewness. The number and types of parameters that are calculated may vary, however, and in some embodiments additional parameters may be used. In one embodiment described with respect to FIG. 6, for example, parameters associated with voltage, local activation time, and fractionation may be used.

Referring back to FIG. 2, method 200 further includes generating 204 a first cumulative map from a first dataset, and generating 206 a second cumulative map from a second dataset. The first dataset includes electrical parameter data for each vertex in the isolated arrhythmogenic substrate, and the second dataset includes additional parameter data for each vertex in the isolated arrhythmogenic substrate. Generating 204 the first cumulative map, and generating 206 the second cumulative map are described below in detail.

Figure 5:
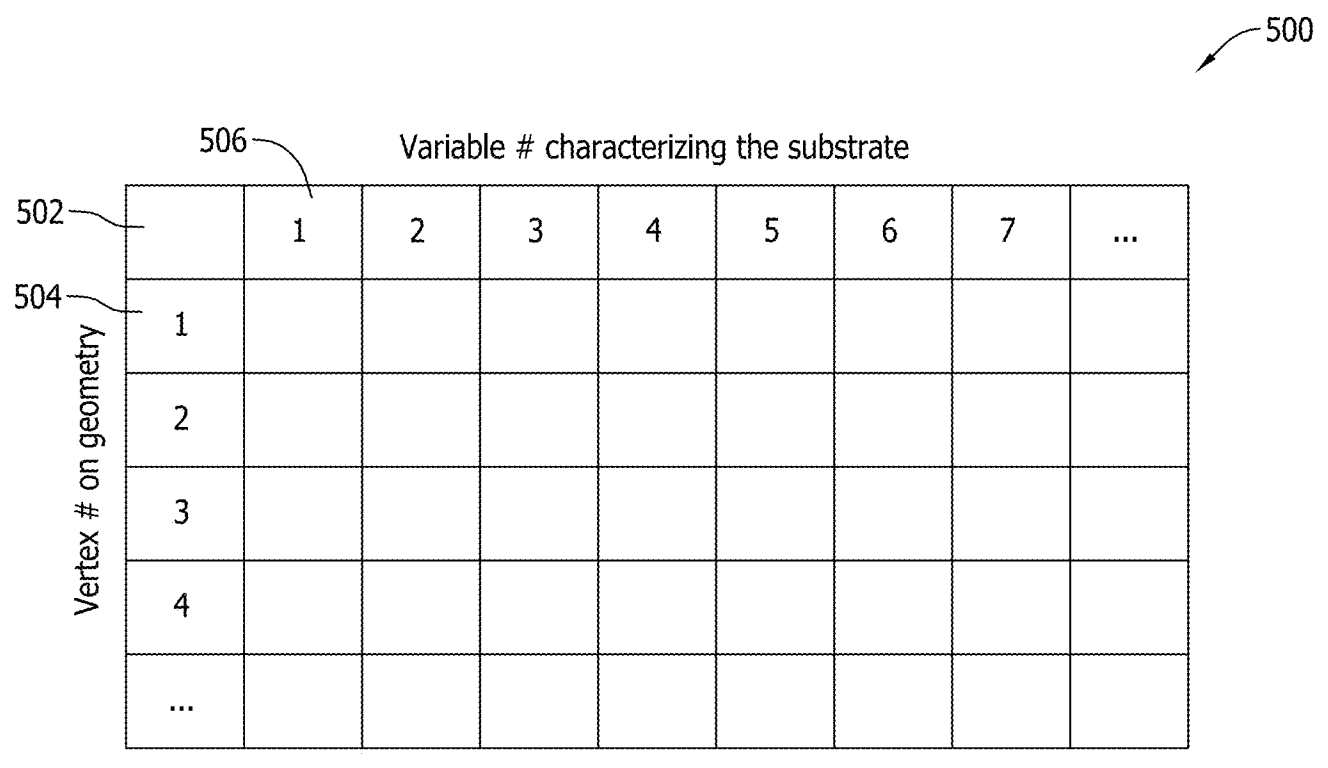

FIG. 5 is a diagram 500 illustrating an example dataset 502 that may be used for the first dataset (including electrical parameter data) and/or the second dataset (including additional parameter data). Dataset 502 includes a plurality of rows 504 and a plurality of columns 506. In this embodiment, each row 504 corresponds to a different vertex, and each column 506 corresponds to a particular electrical data parameter or additional parameter for each vertex. Dataset 502 is merely an example, and is provided to illustrate generating 204, 206 the first and second cumulative maps. Those of skill in the art will appreciate that dataset 502 may have any suitable format.

Figure 6:
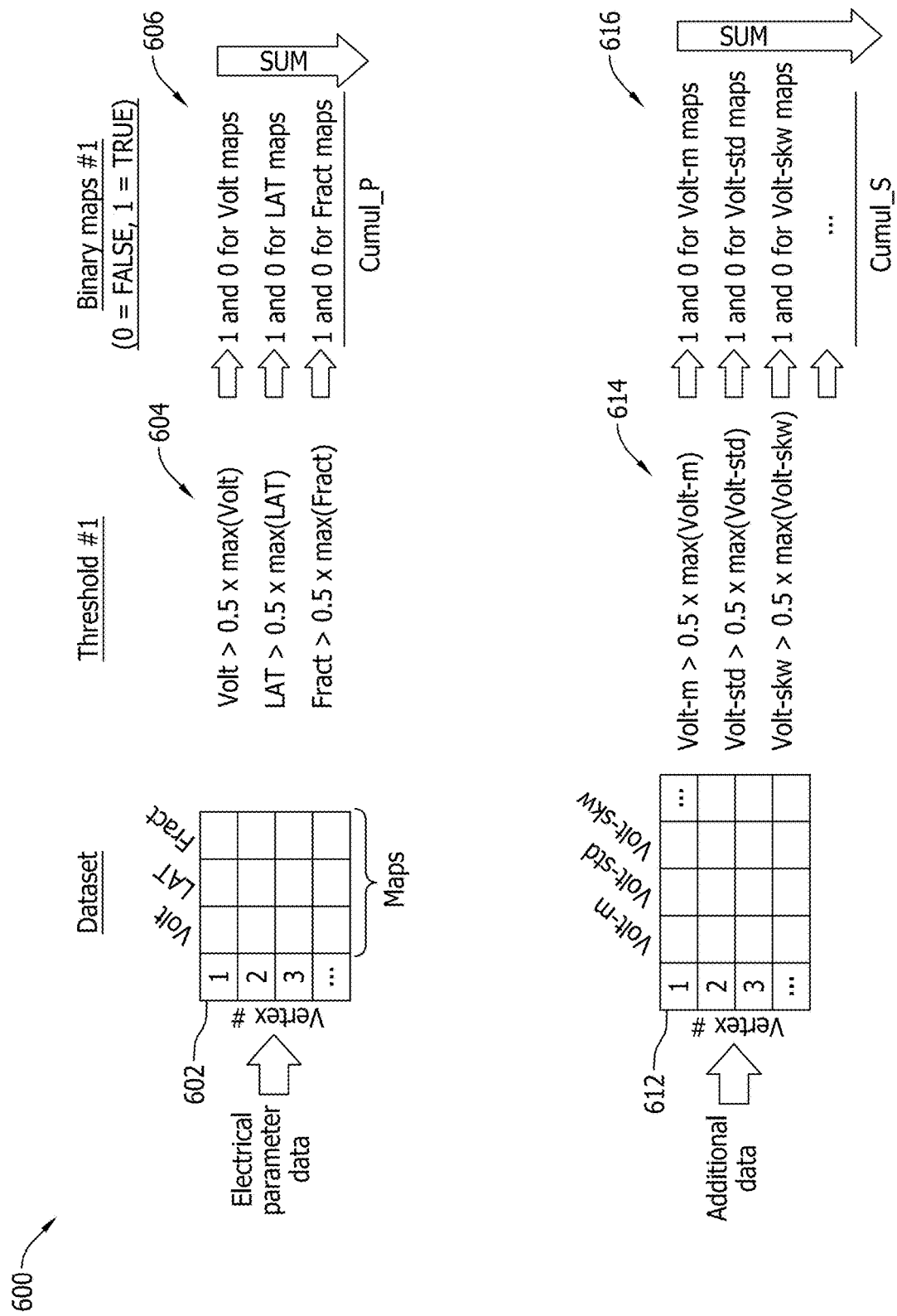
FIG. 6 is a diagram illustrating generation of a first cumulative map and a second cumulative map.

FIG. 6 is a diagram 600 illustrating generating 204 the first cumulative map and generating 206 the second cumulative map. In the example shown in FIG. 6, a first dataset 602 includes electrical data parameter values of voltage, local activation time, and fractionation for each vertex in the isolated arrhythmogenic substrate. To generate 204 the first cumulative map, a first thresholding operation is applied to each value in first dataset 602. Specifically, for each vertex in first dataset 602, values for each type of electrical data parameter are compared to a respective threshold 604. Based on the comparison, a binary map 606 sets values below or equal to a threshold equal to 0, and sets values above the threshold equal to 1. For example, the threshold for a particular electrical data parameter (e.g., voltage) may be 50% of the maximum voltage value in first dataset 602.

In this example, the threshold for each electrical data parameter is set at 50% of the maximum value for that parameter. However, those of skill in the art will appreciate that any suitable threshold may be used, and thresholds may be set at different levels for different electrical data parameters (e.g., the threshold for voltage may be 50% of the maximum voltage, and the threshold for fractionation may be 75% of the maximum fractionation). Further, the thresholds may be preset values, or may be adjusted during the procedure (e.g., upon request by the clinician).

For example, the following Table 1 is an example first data set 602 for eleven vertices:

TABLE 1

| Vertex_Num | Rest_Perf | Stress_Perf | Ischem | Voltage | Fractionation | LAT |
|---|---|---|---|---|---|---|
| 1 | 83.65 | 80.99 | 2.65 | 3.22 | 2.00 | 49.27 |
| 2 | 83.50 | 79.32 | 4.18 | 3.22 | 2.00 | 49.27 |
| 3 | 65.78 | 58.23 | 7.54 | 3.08 | 2.34 | 41.71 |
| 4 | 53.66 | 48.22 | 5.44 | 2.01 | 2.83 | 30.77 |
| 5 | 76.92 | 67.08 | 9.83 | 2.45 | 1.91 | 28.78 |
| 6 | 76.41 | 63.50 | 12.90 | 2.69 | 1.86 | 31.09 |

TABLE 1-continued

| Vertex_Num | Rest_Perf | Stress_Perf | Ischem | Voltage | Fractionation | LAT |
|---|---|---|---|---|---|---|
| 7 | 32.33 | 19.00 | 13.33 | 0.74 | 4.00 | 35.08 |
| 8 | 45.78 | 43.77 | 2.00 | 1.14 | 3.81 | 39.94 |
| 9 | 53.77 | 35.43 | 18.34 | 1.45 | 3.64 | 37.31 |
| 10 | 21.44 | 9.04 | 12.40 | 0.69 | 4.79 | 36.01 |
| 11 | 10.11 | 2.45 | 7.65 | 0.31 | 5.00 | 34.91 |

After comparing values for each electrical data parameter in Table 1 to a respective threshold 604 that is 50% of the maximum value for the associated electrical data parameter, Table 2 is the binary map 606 that is generated:

TABLE 2

| Vertex_Num | Rest_Perf | Stress_Perf | Ischem | Voltage | Fractionation | LAT |
|---|---|---|---|---|---|---|
| 1 | 1 | 1 | 0 | 1 | 0 | 1 |
| 2 | 1 | 1 | 0 | 1 | 0 | 1 |
| 3 | 1 | 1 | 0 | 1 | 0 | 1 |
| 4 | 1 | 1 | 0 | 1 | 1 | 1 |
| 5 | 1 | 1 | 1 | 1 | 0 | 1 |
| 6 | 1 | 1 | 1 | 1 | 0 | 1 |
| 7 | 0 | 0 | 1 | 1 | 1 | 1 |
| 8 | 1 | 1 | 0 | 0 | 1 | 1 |
| 9 | 1 | 0 | 1 | 0 | 1 | 1 |
| 10 | 0 | 0 | 1 | 0 | 1 | 1 |
| 11 | 0 | 0 | 0 | 0 | 1 | 1 |

Once each electrical data parameter value in first dataset 206 is set equal to 0 or 1, for each vertex, the electrical data parameter values are summed to generate 204 the first cumulative map. For example, if a particular vertex has a value of 1 for voltage, a value of 0 for local activation time, and a value of 1 for fractionation, the summed value for that particular vertex will be 2. Thus, in the first cumulative map, each vertex has an associated integer value calculated by summing the binary map results for that vertex. The cumulative map is a one-dimensional vector with one value for each vertex. For example, the following Table 3 is the cumulative map generated from Table 2:

TABLE 3

| Vertex_Num | Cumul_P |
|---|---|
| 1 | 4 |
| 2 | 4 |
| 3 | 4 |
| 4 | 5 |
| 5 | 5 |
| 6 | 5 |
| 7 | 4 |
| 8 | 4 |
| 9 | 4 |
| 10 | 3 |
| 11 | 2 |

The second cumulative map is generated 206 similarly using additional data parameters that are derived from the electrical data parameters. Specifically, in the example shown in FIG. 6, a second dataset 612 includes additional data parameters values for at least mean voltage, voltage standard deviation, and voltage skewness for each vertex in the isolated arrhythmogenic substrate. To generate 206 the second cumulative map, a second thresholding operation is applied to each value in second dataset 612. Specifically, for each vertex in second dataset 612, values for each type of additional data parameter are compared to a respective threshold 614. Based on the comparison, a binary map 616 sets values below or equal to a threshold equal to 0, and sets values above the threshold equal to 1. For example, the threshold for a particular additional data parameter (e.g., mean voltage) may be 50% of the maximum mean voltage value in second dataset 612.

In this example, the threshold for each additional data parameter is set at 50% of the maximum value for that parameter. However, those of skill in the art will appreciate that any suitable threshold may be used, and thresholds may be set at different levels for different additional data parameters (e.g., the threshold for mean voltage may be 50% of the maximum mean voltage, and the threshold for voltage standard deviation may be 75% of the maximum voltage standard deviation). Further, the thresholds may be preset values, or may be adjusted during the procedure (e.g., upon request by the clinician).

For example, the following Table 4 is an example second data set 612:

TABLE 4

| Vertex_Num | Mean_Volt | STD_Volt | Skew_Volt | Mean_LAT | STD_LAT | Skew_LAT | Mean_Fract | STD_Fract | Skew_Fract |
|---|---|---|---|---|---|---|---|---|---|
| 1 | 3.17 | 0.09 | −1.68 | 28.36 | 5.13 | 1.68 | 2.12 | 0.23 | 1.68 |
| 2 | 3.10 | 0.19 | −2.27 | 30.66 | 6.51 | 0.81 | 2.19 | 0.30 | 0.89 |
| 3 | 3.00 | 0.23 | −1.09 | 34.13 | 7.64 | 0.10 | 2.25 | 0.37 | 0.49 |
| 4 | 2.87 | 0.29 | −0.65 | 37.34 | 7.26 | −0.3 | 2.19 | 0.40 | 0.54 |
| 5 | 2.73 | 0.35 | −0.51 | 40.60 | 5.83 | −0.75 | 2.06 | 0.44 | 0.82 |
| 6 | 2.78 | 0.41 | 0.02 | 41.29 | 4.38 | −0.17 | 1.72 | 0.47 | 0.84 |
| 7 | 2.83 | 0.44 | −0.13 | 39.26 | 4.66 | 0.15 | 1.45 | 0.29 | 0.04 |
| 8 | 2.78 | 0.44 | −0.10 | 37.93 | 4.65 | −0.64 | 1.35 | 0.24 | 0.27 |
| 9 | 2.69 | 0.43 | −0.37 | 37.84 | 5.38 | −0.52 | 1.36 | 0.23 | 0.02 |
| 10 | 2.49 | 0.44 | −0.41 | 38.72 | 5.94 | −0.28 | 1.52 | 0.28 | −0.09 |
| 11 | 2.28 | 0.44 | −0.32 | 40.24 | 7.78 | 0.45 | 1.65 | 0.24 | 0.04 |

Because some of the values are negative in Table 4, in some embodiments, for additional data parameters with at least some negative values, the values are adjusted such that the lowest value (i.e., the most negative value) is set to zero. For example, the following Table 5 is generated when making that adjustment to Table 4:

TABLE 5

| Vertex_Num | Mean_Volt | STD_Volt | Skew_Volt | Mean_LAT | STD_LAT | Skew_LAT | Mean_Fract | STD_Fract | Skew_Fract |
|---|---|---|---|---|---|---|---|---|---|
| 1 | 3.17 | 0.09 | 0.59 | 28.36 | 5.13 | 2.43 | 2.12 | 0.23 | 1.77 |
| 2 | 3.1 | 0.19 | 0 | 30.66 | 6.51 | 1.56 | 2.19 | 0.3 | 0.98 |
| 3 | 3 | 0.23 | 1.18 | 34.13 | 7.64 | 0.85 | 2.25 | 0.37 | 0.58 |
| 4 | 2.87 | 0.29 | 1.62 | 37.34 | 7.26 | 0.45 | 2.19 | 0.4 | 0.63 |
| 5 | 2.73 | 0.35 | 1.76 | 40.6 | 5.83 | 0 | 2.06 | 0.44 | 0.91 |
| 6 | 2.78 | 0.41 | 2.29 | 41.29 | 4.38 | 0.58 | 1.72 | 0.47 | 0.93 |
| 7 | 2.83 | 0.44 | 2.14 | 39.26 | 4.66 | 0.9 | 1.45 | 0.29 | 0.13 |
| 8 | 2.78 | 0.44 | 2.17 | 37.93 | 4.65 | 0.11 | 1.35 | 0.24 | 0.36 |
| 9 | 2.69 | 0.43 | 1.9 | 37.84 | 5.38 | 0.23 | 1.36 | 0.23 | 0.11 |
| 10 | 2.49 | 0.44 | 1.86 | 38.72 | 5.94 | 0.47 | 1.52 | 0.28 | 0 |
| 11 | 2.28 | 0.44 | 1.95 | 40.24 | 7.78 | 1.2 | 1.65 | 0.24 | 0.13 |

After comparing values for each additional data parameter in Table 5 to a respective threshold 614 that is 50% of the maximum value for the associated additional data parameter, Table 6 is the binary map 616 that is generated:

TABLE 6

| Vertex_Num | Mean_Volt | STD_Volt | Skew_Volt | Mean_LAT | STD_LAT | Skew_LAT | Mean_Fract | STD_Fract | Skew_Fract |
|---|---|---|---|---|---|---|---|---|---|
| 1 | 1 | 0 | 0 | 1 | 1 | 1 | 1 | 0 | 1 |
| 2 | 1 | 0 | 0 | 1 | 1 | 1 | 1 | 1 | 1 |
| 3 | 1 | 1 | 1 | 1 | 1 | 0 | 1 | 1 | 0 |
| 4 | 1 | 1 | 1 | 1 | 1 | 0 | 1 | 1 | 0 |
| 5 | 1 | 1 | 1 | 1 | 1 | 0 | 1 | 1 | 1 |
| 6 | 1 | 1 | 1 | 1 | 1 | 0 | 1 | 1 | 1 |
| 7 | 1 | 1 | 1 | 1 | 1 | 0 | 1 | 1 | 0 |
| 8 | 1 | 1 | 1 | 1 | 1 | 0 | 1 | 1 | 0 |
| 9 | 1 | 1 | 1 | 1 | 1 | 0 | 1 | 0 | 0 |
| 10 | 1 | 1 | 1 | 1 | 1 | 0 | 1 | 1 | 0 |
| 11 | 1 | 1 | 1 | 1 | 1 | 0 | 1 | 1 | 0 |

Once each additional data parameter value in second dataset 612 is set equal to 0 or 1, for each vertex, the additional data parameter values are summed to generate 206 the second cumulative map. Thus, in the second cumulative map, each vertex has an associated integer value calculated by summing the binary map results for that vertex. High values of standard deviation and/or highly skewed data will generally occur at border zones. Thus, the second cumulative map will generally identify areas of high variability along the border zones. The second cumulative map is also a one-dimensional vector with one value for each vertex. For example, the following Table 7 is the cumulative map generated from Table 6:

TABLE 7

| Vertex_Num | Cumul_S |
|---|---|
| 1 | 6 |
| 2 | 7 |
| 3 | 7 |
| 4 | 7 |
| 5 | 8 |
| 6 | 8 |
| 7 | 7 |
| 8 | 7 |
| 9 | 6 |
| 10 | 7 |
| 11 | 7 |

Figure 7:
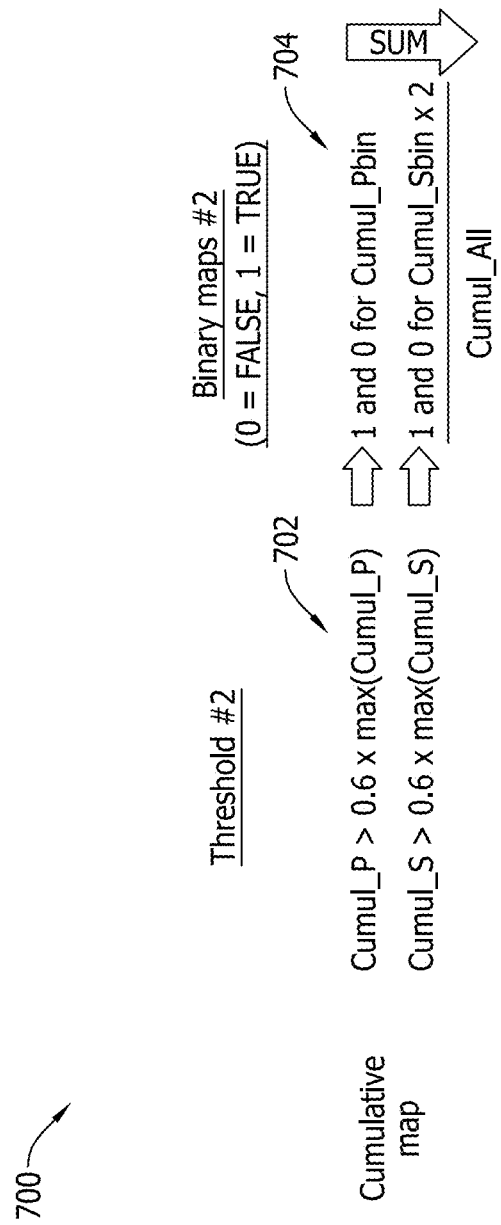
FIG. 7 is a diagram illustrating generation of a third cumulative map.

Referring back to FIG. 2, method 200 further includes generating 208 a third cumulative map from the first and second cumulative maps. FIG. 7 is a diagram 700 illustrating generating 208 the third cumulative map. In one embodiment, to generate 208 the third cumulative map, a third thresholding operation is applied to each value in the first cumulative map and the second cumulative map. Specifically, for each vertex, the first cumulative map values and the second cumulative map values are compared to respective thresholds 702. Based on the comparison, a binary map 704 sets values below or equal to the threshold equal to 0, and sets values above the threshold equal to 1. For example, the predetermined threshold for the first cumulative map may be 60% of the maximum value in the first cumulative map.

In this example, the threshold for the first and second cumulative maps is set at 60% of the maximum value for the associated map. However, those of skill in the art will appreciate that any suitable threshold may be used, and thresholds may be set at different levels for the different cumulative maps (e.g., the threshold for the first cumulative map may be 50% of the maximum value, and the threshold for the second cumulative map may be 60% of the maximum value). Further, the thresholds may be preset values, or may be adjusted during the procedure (e.g., upon request by the clinician).

In one embodiment, to distinguish the second cumulative map from the first cumulative map, the value for the binary map corresponding to the second cumulative map is multiplied by 2 (i.e., such that each vertex in the binary map corresponding to the second cumulative map value of 0 or 2 after the third thresholding operation).

For example, the following Table 8 is a binary map 704 generated from the first cumulative map of Table 3, and the following Table 9 is a binary map 704 generated from the second cumulative map of Table 7 (including the multiplication by 2):

TABLE 8

| Vertex_Num | Cumul_P |
|---|---|
| 1 | 1 |
| 2 | 1 |
| 3 | 1 |
| 4 | 1 |
| 5 | 1 |
| 6 | 1 |
| 7 | 1 |
| 8 | 1 |
| 9 | 1 |
| 10 | 0 |
| 11 | 0 |

TABLE 9

| Vertex_Num | Cumul_S |
|---|---|
| 1 | 2 |
| 2 | 2 |
| 3 | 2 |
| 4 | 2 |
| 5 | 2 |
| 6 | 2 |
| 7 | 2 |
| 8 | 2 |
| 9 | 2 |
| 10 | 2 |
| 11 | 2 |

Once each value for the first cumulative binary map 704 is set to 0 or 1, and each value for the second cumulative binary map 704 is set to 0 or 2, for each vertex, the binary map values are summed to generate 208 the third cumulative map. For example, if a particular vertex has a value of 1 for the first cumulative binary map 704 and a value of 2 for the second cumulative binary map 704, the summed value for that particular vertex will be 3.

Thus, in the third cumulative map, each vertex has an associated integer value of 0, 1, 2, or 3. A value of 0 indicates the values were 0 for both binary maps 704, a value of 1 indicates the value was 1 for the first cumulative binary map 704 and 0 for the second cumulative binary map 704, a values of 2 indicates the value was 0 for the first cumulative binary map and 2 for the second cumulative binary map, and a value of 3 indicates the value was 1 for the first cumulative binary map and 2 for the second cumulative binary map.

For example, the following Table 10 is a third cumulative map generated from Tables 8 and 9:

TABLE 10

| Vertex_Num | Cumul_All |
|---|---|
| 1 | 3 |
| 2 | 3 |
| 3 | 3 |
| 4 | 3 |
| 5 | 3 |
| 6 | 3 |
| 7 | 3 |
| 8 | 3 |
| 9 | 3 |
| 10 | 2 |
| 11 | 2 |

Referring back to FIG. 2, method 200 further includes displaying 210 the third cumulative map on the three-dimensional geometry. Because the third cumulative map includes contributions from the first and second cumulative maps, displaying 210 the third cumulative map on the three-dimensional map indicates areas of high variability in the arrhythmogenic substrate. The displayed map enables a clinician to quickly and easily identify potential ablation locations.

FIGS. 8A-8C illustrate a comparison between existing ablation determination techniques and the systems and methods described herein. Specifically, FIG. 8A shows a three-dimensional geometry 802 without any ablation information. FIG. 8B shows the same geometry 802 post-procedurally, with actual ablation sites and fractionation locations identified. In this example, the ablation was performed by a clinician without using the systems and methods described herein.

FIG. 8C shows the same geometry 802 including various regions of interest 804 that are identified in accordance with the systems and methods described herein. Regions of interest 804 have high electrical variability, as identified by the first cumulative map, the second cumulative map, or both the first and second cumulative maps. Specifically, regions of interest 804 includes first regions of interest 808 identified by only the first cumulative map, second regions of interest 806 identified by only the second cumulative map, and third regions of interest 810 identified by both the first and second cumulative maps.

For illustration, the ablation sites and fractionation locations from FIG. 8B are overlaid onto geometry 802 shown in FIG. 8C. As demonstrated by FIG. 8B, at least some of the potential ablation sites identified using the systems and methods described correspond to the actual ablation sites, but other potential ablation sites identified in FIG. 8C fall outside of the clinician-selected actual ablation sites of FIG. 8B. Accordingly, ablating per the identified potential ablation sites may generate improved results relative to the techniques used in FIG. 8B.

The systems and methods described herein are directed to identifying potential ablation sites using electrical parameter data. A method includes geometrically isolating an arrhythmogenic substrate in a three-dimensional geometry. The method further includes generating a first cumulative map from a first dataset including electrical parameter data for each vertex in the isolated arrhythmogenic substrate, and generating a second cumulative map from a second dataset including additional data for each vertex. The method further includes generating a third cumulative map from the first and second cumulative maps, and displaying the third cumulative map on the three-dimensional geometry to facilitate identifying potential ablation sites.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A method for identifying potential ablation sites, the method comprising:
    sensing, using at least one sensor of a mapping and/or imaging device, sensor data from a subject;
    transmitting the sensed sensor data from the mapping and/or imaging device to a computing device;
    generating, using the computing device, a three-dimensional geometry that includes a plurality of vertices, the three-dimensional geometry generated from the sensed sensor data;
    geometrically isolating, using the computing device, an arrhythmogenic substrate in the three-dimensional geometry;
    generating, using the computing device, a first cumulative map from a first dataset, the first dataset including electrical parameter data for each vertex of the plurality of vertices that is in the isolated arrhythmogenic substrate;
    deriving, using the computing device, for each vertex of the plurality of vertices that is in the isolated arrhythmogenic substrate, additional data from the electrical parameter data;
    generating, using the computing device, a second cumulative map from a second dataset, the second dataset including the derived additional data;
    generating, using the computing device, a third cumulative map from the first and second cumulative maps; and
    displaying, using the computing device, the third cumulative map on the three-dimensional geometry to facilitate identifying the potential ablation sites.

2. The method of claim 1, wherein the electrical parameter data includes at least one of voltage data, local activation time data, and fractionation data.

3. The method of claim 1, wherein the additional data includes at least one of mean voltage data, voltage standard deviation data, voltage skewness data, mean local activation time data, local activation time standard deviation data, local activation time skewness data, mean fractionation data, fractionation standard deviation data, and fractionation skewness data.

4. The method of claim 1, further comprising:
    determining a mean voltage value for each of the plurality of vertices, wherein geometrically isolating an arrhythmogenic substrate comprises discarding vertices of the plurality of vertices from the three-dimensional geometry that have a mean voltage value above a predetermined threshold.

5. The method of claim 1, wherein generating a first cumulative map comprises:
- comparing values of the electrical parameter data for each vertex of the plurality of vertices in the isolated arrhythmogenic substrate to an associated threshold;
- assigning each electrical parameter data value equal to 0 or 1 based on the comparison; and
- summing the assigned electrical parameter data values for each vertex of the plurality of vertices in the isolated arrhythmogenic substrate.

6. The method of claim 1, wherein generating a second cumulative map comprises:
- comparing values of the additional data for each vertex of the plurality of vertices in the isolated arrhythmogenic substrate to an associated threshold;
- assigning each additional data value equal to 0 or 1 based on the comparison; and
- summing the assigned additional data values for each vertex of the plurality of vertices in the isolated arrhythmogenic substrate.

7. The method of claim 1, wherein generating a third cumulative map comprises:
- comparing values of the first cumulative map and values of the second cumulative map for each vertex of the plurality of vertices in the isolated arrhythmogenic substrate to an associated threshold;
- assigning each first and second cumulative map value equal to 0, 1, or 2 based on the comparison; and
- summing the assigned first and second cumulative map values for each vertex of the plurality of vertices in the isolated arrhythmogenic substrate.

8. The method of claim 1, further comprising performing an ablation procedure at one of the potential ablation sites.

9. A system for identifying potential ablation sites, the system comprising:
- a mapping and/or imaging device comprising at least one sensor, the at least one sensor configured to sense sensor data from a subject;
- a computing device communicatively coupled to the mapping and/or imaging device, the computing device comprising:
  - a memory device; and
  - a processor communicatively coupled to the memory device, the processor configured to:
    - receive the sensed sensor data from the mapping and/or imaging device;
    - generate, using the sensed sensor data, a three-dimensional geometry that includes a plurality of vertices;
    - geometrically isolate an arrhythmogenic substrate in the three-dimensional geometry;
    - generate a first cumulative map from a first dataset, the first dataset including electrical parameter data for each vertex of the plurality of vertices that is in the isolated arrhythmogenic substrate;
    - derive, for each vertex of the plurality of vertices that is in the isolated arrhythmogenic substrate, additional data from the electrical parameter data;
    - generate a second cumulative map from a second dataset, the second dataset including the derived additional data;
    - generate a third cumulative map from the first and second cumulative maps; and
    - display the third cumulative map on the three-dimensional geometry to facilitate identifying the potential ablation sites.

10. The system of claim 9, wherein the electrical parameter data includes at least one of voltage data, local activation time data, and fractionation data.

11. The system of claim 9, wherein the additional data includes at least one of mean voltage data, voltage standard deviation data, voltage skewness data, mean local activation time data, local activation time standard deviation data, local activation time skewness data, mean fractionation data, fractionation standard deviation data, and fractionation skewness data.

12. The system of claim 9, wherein the processor is further configured to determine a mean voltage value for each of the plurality of vertices, and wherein to geometrically isolate an arrhythmogenic substrate, the processor is configured to discard vertices of the plurality of vertices from the three-dimensional geometry that have a mean voltage value above a predetermined threshold.

13. The system of claim 9, wherein to generate a first cumulative map, the processor is configured to:
- compare values of the electrical parameter data for each vertex of the plurality of vertices in the isolated arrhythmogenic substrate to an associated threshold;
- assign each electrical parameter data value equal to 0 or 1 based on the comparison; and
- sum the assigned electrical parameter data values for each vertex of the plurality of vertices in the isolated arrhythmogenic substrate.

14. The system of claim 9, wherein to generate a second cumulative map, the processor is configured to:
- compare values of the additional data for each vertex of the plurality of vertices in the isolated arrhythmogenic substrate to an associated threshold;
- assign each additional data value equal to 0 or 1 based on the comparison; and
- sum the assigned additional data values for each vertex of the plurality of vertices in the isolated arrhythmogenic substrate.

15. The system of claim 9, wherein to generate a third cumulative map, the processor is configured to:
- compare values of the first cumulative map and values of the second cumulative map for each vertex of the plurality of vertices in the isolated arrhythmogenic substrate to an associated threshold;
- assign each first and second cumulative map value equal to 0, 1, or 2 based on the comparison; and
- sum the assigned first and second cumulative map values for each vertex of the plurality of vertices in the isolated arrhythmogenic substrate.

16. Non-transitory computer-readable media having computer-executable instructions thereon, wherein when executed by a processor of a computing device, cause the processor of the computing device to:
- sense, using at least one sensor of a mapping and/or imaging device communicatively coupled to the computing device, sensor data from a subject;
- generate, from the sensed sensor data, a three-dimensional geometry that includes a plurality of vertices;
- geometrically isolate an arrhythmogenic substrate in the three-dimensional geometry;
- generate a first cumulative map from a first dataset, the first dataset including electrical parameter data for each vertex of the plurality of vertices that is in the isolated arrhythmogenic substrate;
- derive, for each vertex of the plurality of vertices that is in the isolated arrhythmogenic substrate, additional data from the electrical parameter data;

generate a second cumulative map from a second dataset, the second dataset including the derived additional data;

generate a third cumulative map from the first and second cumulative maps; and display the third cumulative map on the three-dimensional geometry to facilitate identifying potential ablation sites.

17. The non-transitory computer-readable media of claim 16, wherein the electrical parameter data includes at least one of voltage data, local activation time data, and fractionation data.

18. The non-transitory computer-readable media of claim 16, wherein the additional data includes at least one of mean voltage data, voltage standard deviation data, voltage skewness data, mean local activation time data, local activation time standard deviation data, local activation time skewness data, mean fractionation data, fractionation standard deviation data, and fractionation skewness data.

19. The non-transitory computer-readable media of claim 16, wherein the computer-executable instructions are configured to cause the processor to determine a mean voltage value for each of the plurality of vertices, and wherein to geometrically isolate an arrhythmogenic substrate, the computer-executable instructions are configured to cause the processor to discard vertices of the plurality of vertices from the three-dimensional geometry that have a mean voltage value above a predetermined threshold.

20. The non-transitory computer-readable media of claim 16, wherein to generate a first cumulative map, the computer-executable instructions are configured to cause the processor to:

compare values of the electrical parameter data for each vertex of the plurality of vertices in the isolated arrhythmogenic substrate to an associated threshold;

assign each electrical parameter data value equal to 0 or 1 based on the comparison; and sum the assigned electrical parameter data values for each vertex of the plurality of vertices in the isolated arrhythmogenic substrate.

* * * * *